United States Patent [19]
Westin

[11] Patent Number: 5,667,509
[45] Date of Patent: Sep. 16, 1997

[54] RETRACTABLE SHIELD APPARATUS AND METHOD FOR A BONE DRILL

[76] Inventor: Craig D. Westin, 1383 Arlington Dr., Salt Lake City, Utah 84103

[21] Appl. No.: 399,157

[22] Filed: Mar. 2, 1995

[51] Int. Cl.⁶ ............................ A61B 17/32; A61B 17/16
[52] U.S. Cl. .................... 606/80; 606/96; 606/170
[58] Field of Search .................. 606/80, 86, 87, 606/79, 96, 170

[56] References Cited

U.S. PATENT DOCUMENTS

| | | | |
|---|---|---|---|
| 3,682,177 | 8/1972 | Ames et al. | 606/80 |
| 4,111,208 | 9/1978 | Leuenberger | 606/80 |
| 4,362,161 | 12/1982 | Reimels et al. | 606/80 |
| 4,649,919 | 3/1987 | Thimsen et al. | 606/80 |
| 5,049,150 | 9/1991 | Cozad | 606/96 |
| 5,207,681 | 5/1993 | Ghadjar et al. | 606/96 |
| 5,269,794 | 12/1993 | Rexroth | 606/80 |
| 5,527,331 | 6/1996 | Kresch et al. | 606/170 |
| 5,529,580 | 6/1996 | Kusunoki et al. | 606/170 |

FOREIGN PATENT DOCUMENTS

| | | | |
|---|---|---|---|
| 1124938 | 11/1984 | U.S.S.R. | 606/80 |
| 1465033 | 3/1989 | U.S.S.R. | 606/80 |

*Primary Examiner*—Michael Buiz
*Assistant Examiner*—Julian W. Woo
*Attorney, Agent, or Firm*—J. Winslow Young

[57] ABSTRACT

A bone drill enclosed by a retractable sheath, the sheath having bevel points at its distal end for engaging the bone and a spring at its proximal end for resiliently urging the distal end against the surface of the bone while allowing the sheath to be retracted as the drill penetrates the bone. The sheath telescopically shields the bone drill to protect the adjacent tissue from the rotating bone drill. Indicia on the sheath provide a visual indication of the depth to which the drill bit has penetrated into the bone by the degree to which the sheath has been retracted as the bone drill penetrates into the bone. The bone drill is configured with a hollow, tubular shaft having an orifice adjacent the drill bit. Suction is applied to the lumen of the bone drill to remove debris generated by the drilling action, the debris being drawn through the orifice.

20 Claims, 3 Drawing Sheets

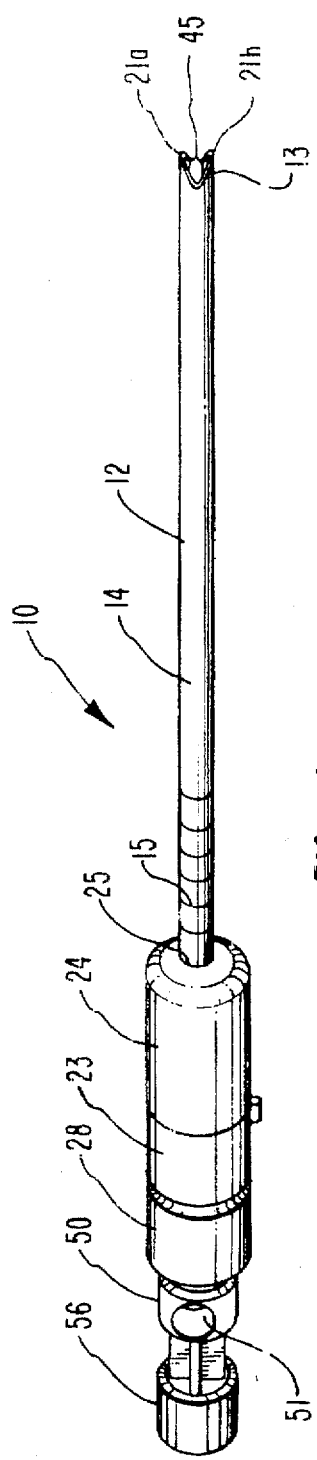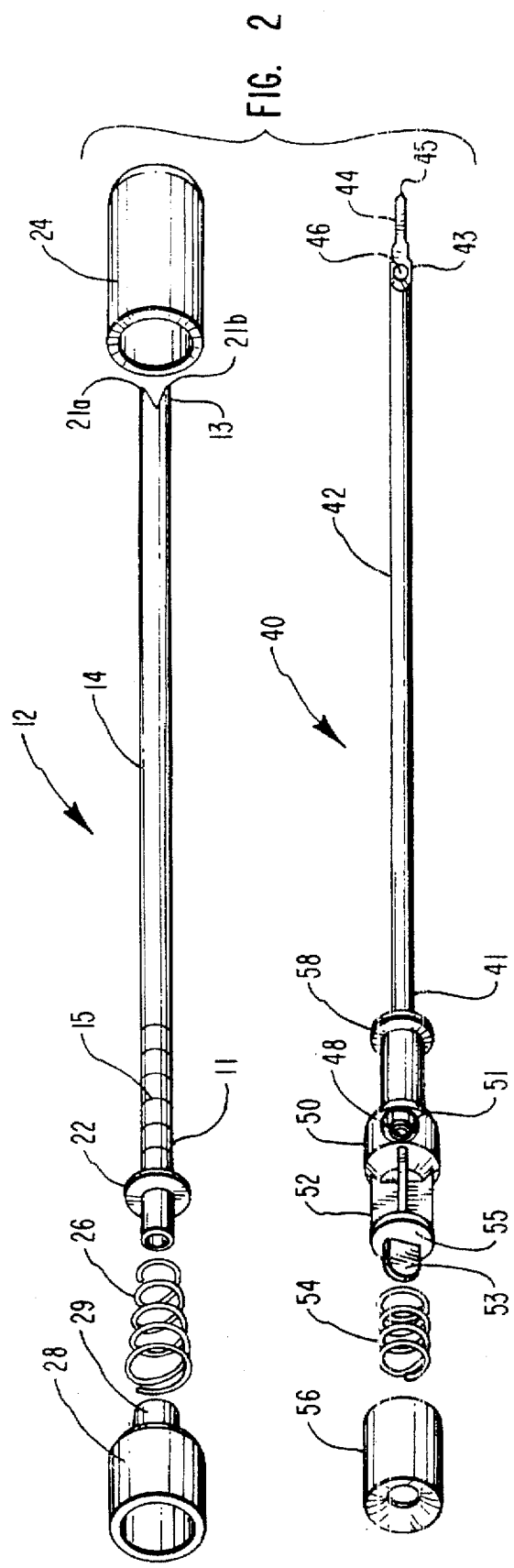

RETRACTABLE SHIELD APPARATUS AND METHOD FOR A BONE DRILL

BACKGROUND

1. Field of the Invention

This invention relates to bone drills and, more particularly, to a unique, retractable, tubular shield apparatus and method for enclosing a bone drill, the shield having a sharpened point for engagement with the bone to both aid in the alignment of the bonedrill and to preclude the bone drill from skidding across the bone surface upon commencement of the drilling operation.

2. The Prior Art

Various medical procedures involve drilling a hole in bone. For example, the procedure for the repair of ligaments and tendons involves the placement of suture anchors in the underlying bone so that the particular ligament or tendon can be reattached to the bone through the use of sutures. Historically, this procedure was accomplished through invasive surgery requiring extended hospitalization, etc. However, the fairly recent advances in arthroscopic surgical techniques have practically eliminated the need for invasive surgery for ligament and tendon repair. The corresponding result from this kind of surgery is that it is now routinely conducted on an outpatient basis. The beneficial result is a significant decrease in the trauma to the patient, a shorter recovery period, reduced scarring, lower costs, and the like.

The current practice of ligament or tendon reattachment involves the implantation of a plurality of suture anchors in the bone at preselected positions relative to the original attachment site of ligament or tendon to the bone. Implantation of the suture anchor customarily requires a hole drilled into the bone to receive the suture anchor. The hole is prepared with a prescribed depth and is drilled with a bone drill having a preselected diameter to produce a hole having the appropriate dimensions. The anchor is embedded in the hole and the ligament or tendon is then secured to the suture anchor using appropriate suturing techniques.

Other surgical procedures involve drilling a plurality of spaced holes in bone for the purpose of increasing the blood supply to that particular area of the bone. However, I have found that the operation of a conventional rotating drill bit near exposed tissue, particularly that encountered in the close confines of an arthroscopic procedure, frequently results in loose ends of the exposed tissue becoming entangled by the rotating drill bit. Another problem I have encountered in my practice as an orthopedic surgeon is that it is extremely difficult to precisely position a hole drilled in a curved surface of the bone, particularly during certain surgical procedures involving the repair of injuries to the knee and the shoulder. This difficulty results from the tip of the drill bit slipping across the curved surface of the bone as the drill is rotated. This problem is especially acute when the hole to be drilled is oriented at an angle other than 90 degrees to the bone surface. A further problem I have encountered in my practice is the production of bone residue that remains after the drilling procedure has been completed.

In view of the foregoing, it would be an advancement in the art to provide a shield for the bone drill apparatus and method whereby the bone drill is shielded to preclude loose tissue from becoming entangled with the rotating bone drill. Another advancement would be to provide a guide for the bone drill, the guide providing a securement mechanism for preventing the tip of the bone drill from slipping across the surface of the bone. An even further advancement would be to provide a bone drill having an evacuation system for removing debris generated during the drilling procedure. Another advancement would be to provide a depth limiting system for controlling or otherwise limiting the depth to which the bone drill is able to penetrate the bone. Another advancement would be to provide a depth gauge as part of the shield to enable the surgeon to determine the depth of penetration of the bone drill into the bone. Another advancement would be to provide an asymmetric tip to the shield as an assist in inserting the bone drill through the tissue and to more securely anchor the tip of the shield to the bone to more accurately position the drill bit against the bone. Such a novel apparatus and method is disclosed and claimed herein.

BRIEF SUMMARY AND OBJECTS OF THE INVENTION

The present invention is a unique, retractable shield for a bone drill. The shield is configured as a rigid, hollow tubular element that encloses the full length of the bone drill. The distal end of the shield is configured with a sharpened double bevel tip which provides a secure engagement of the tip against the bone surface. The shield is spring biased and retractable to allow the bone drill to be extended beyond the end of the shield and thereby penetrate the underlying bone. The extent of retraction of the drill guide provides both a depth gauge and ultimately a limit for the depth of penetration of the bone drill into the bone. The bone drill itself is configured as a hollow, tubular shaft having an inlet orifice located adjacent the drill bit portion of the bone drill. Suction is applied to the drill shaft to suction drilling debris through the orifice and the lumen of the drill shaft.

It is, therefore, a primary object of this invention to provide improvements in bone drills.

Another object of this invention is to provide improvements in the method of drilling into a bone.

Another object of this invention is to provide a guide for a bone drill.

Another object of this invention is to provide a retractable shield for the bone drill.

Another object of this invention is to provide a retractable shield, the distance of retraction representing the depth of penetration of the bone drill.

Another object of this invention is to provide a depth gauge on the shield to provide a visual indication of the depth to which the drill bit has penetrated the bone.

Another object of this invention is to provide a retractable shield having a spring bias to resiliently urge the shield into telescopically enclosing the bone drill.

Another object of this invention is to provide a bone drill system wherein the drill shaft includes a hollow lumen terminating in an orifice adjacent the distal end of the bone drill to accommodate the evacuation of debris generated by the drilling action of the bone drill into the bone.

These and other objects and features of the present invention will become more readily apparent from the following description and appended claims taken in conjunction with the accompanying drawing.

BRIEF DESCRIPTION OF THE DRAWING

FIG. 1 is a perspective view of one presently preferred embodiment of the novel bone drill and retractable shield of this invention;

FIG. 2 is an exploded, perspective view of the bone drill and the retractable shield;

DETAILED DESCRIPTION OF THE PREFERRED EMBODIMENT

Figure 3:
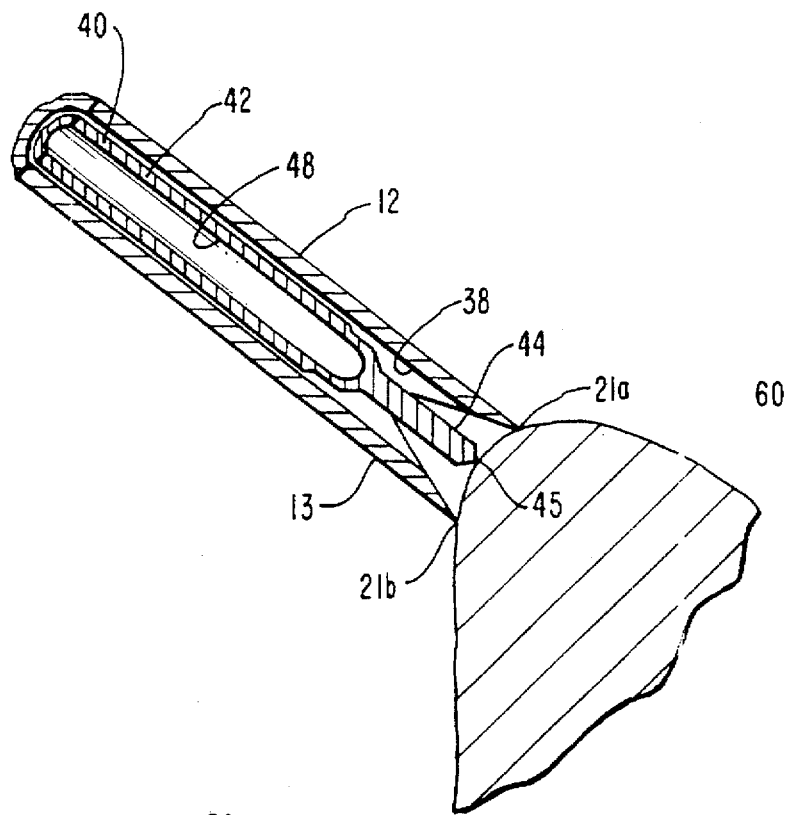
FIG. 3 is a fragmentary, cross-sectional view of the tip of the bone drill and the retractable shield shown in the environment of a portion of bone.

The invention is best understood from the following description taken in conduction with the accompanying drawing wherein like parts are designated by like numerals throughout and with reference to the appended claims.

GENERAL DISCUSSION

The present invention is a unique bone drilling apparatus and method whereby the bone drill is telescopically sheathed inside a retractable shield. The bone drill is an elongated, drill shaft having a drill bit at its distal end. The drill shaft includes a hollow lumen extending between the proximal end an orifice located adjacent the drill bit. Suction is imposed on the hollow drill shaft to remove any debris generated during the drilling operation. The shield protects the rotating bone drill from becoming entangled by adjacent tissue while also enclosing the orifice to more effectively remove debris from the drill site. The distal tip of the shield is configured with a sharpened, double bevel tip to provide an engagement mechanism for releasably securing the tip of the shield against the bone thereby inhibiting the drill bit from skidding relative to the bone surface. The proximal end of the shield includes a spring mechanism for pushing the shield toward the distal end of the bone drill. This spring action helps anchor the distal end of the shield to the bone to enable the bone drill to penetrate the bone at the desired angle and location. As the bone drill penetrates the bone, the shield is retracted by the forward movement of the bone drill to allow the bone drill to penetrate the bone to the depth permitted by the distance to which the drill guide is allowed to retract. Indicia on the proximal end of the shield provide a visual indication of the distance through which the shield has been retracted which is also an indication of the depth of penetration of the drill bit into the bone.

DETAILED DESCRIPTION

Referring now more particularly to FIGS. 1 and 2, the novel bone drill and retractable, shield apparatus of this invention is shown generally at 10 and includes a shield 12 that retractably encases a bone drill 40. Shield 12 is configured as a hollow, sheath 14 having a proximal end 11 and a distal end 13. Sheath 14 includes a pair of bevel points 21a and 21b at distal end 13 and a circumferential collar 22 adjacent proximal end 11. Bevel points 21a and 21b are designed to piercingly engage the surface of a bone 60 (FIGS. 3 and 4) in order to secure the relative position of distal end 13 thereto as will be discussed more fully hereinafter. The apparatus of shield 12 also includes a spacer 23, a housing 24, a spring 26, and an end cap 28. Housing 24 along with spacer 23 is hollow having an axial opening 25 through which sheath 14 extends until collar 22 is in abutment internally with the bottom of housing 24. Spring 26 is mounted between collar 22 and end cap 28 when end cap 28 is secured to housing 24. A tubular boss 29 extends coaxially from the face of end cap 28 and serves as a retainer for spring 26 as well as being an abutment surface for the end of sheath 14 when distal end 13 of sheath 14 is pressed against bone 60 causing spring 26 to be compressed.

Bone drill 40 is configured as a tubular drill shaft 42 having a proximal end 41 and a distal end 43. A drill bit 44 extends coaxially from distal end 43 and terminates in a sharpened drill tip 45. An orifice 46 is located at distal end 43 at a position immediately aft of drill bit 44 and provides the distal opening to the interior of a lumen 48 (FIGS. 3 and 4) of tubular shaft 42. Drill shaft 42 is mounted to a hub 50. Hub 50 is configured to secure bone drill 40 to a conventional drill motor (not shown) which is used to rotate bone drill 40. Hub 50 includes a connector 52, a drill spring 54 and an end cap 56. The proximal end of connector 52 includes a coupling 53 which extends coaxially from connector 52 and provides the necessary engagement mechanism for rotatably coupling bone drill 40 to the drill motor. Connector 52 also includes a circumferential base 55 surrounding coupling 53 with base 55 forming an abutment surface on the proximal end of connector 52 and against which spring 54 is resiliently urged when end cap 56 is pressed against spring 54.

Connector 52 also includes a side port 51 which provides fluid communication with lumen 48 of drill shaft 42. The distal end of hub 50 terminates in an outwardly extending lip 58 which serves as the engagement surface for contacting a similar surface (not shown) located in the base of socket 28. At this point it should be noted that the apparatus of hub 50 may be suitably configured to be used with any preselected drill motor and evacuation system (not shown) since several configurations of these devices are commercially available. Clearly, of course, my novel bone drill and shield 10 is therefore not limited to any specific drill motor and evacuation system.

Figure 4:
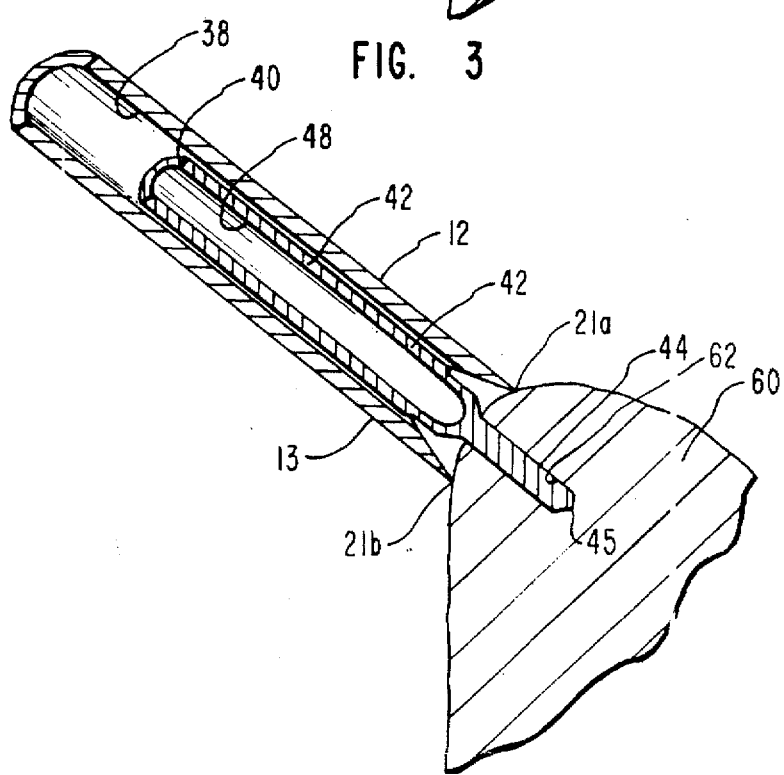
FIG. 4 is the fragmentary, cross-sectional view of FIG. 3 shown with the bone drill penetrated into the bone.

Referring now to FIGS. 3 and 4, distal end 13 of sheath 14 is shown with bevel points 21a and 21b in engagement with the surface of bone 60. As shown in FIG. 3, drill tip 45 is also pressed against bone 60. Advantageously, the resiliency of spring 26 (FIG. 2) allows drill shaft 42 to be telescopically pushed incrementally into the body of sheath 14 thereby accommodating the engagement of bevel points 21a and 21b securely with the surface of bone 60. With bevel points 21a and 21b securely engaged against bone 60, the drill motor (not shown) is activated causing drill tip 45 to penetrate bone 60. As drill bit 44 penetrates bone 60, sheath 14 is retracted relative to bone drill 40. Or, to state it more accurately, drill bit 44 extends beyond distal end 13 causing sheath 14 to compress spring 26 (FIG. 2) thereby resulting in the aforesaid retraction of sheath 14 relative to the forward extension of drill bit 44. The depth of penetration of drill bit 44 into bone 60 is limited by the total available distance between the proximal end of sheath 14 and the end of tubular boss 29. The actual depth of penetration is indicated visually by the passage of indicia 15 inside housing 24. During this retraction of sheath 14, bevel points 21a and 21b are held securely in engagement with bone 60 by the resiliency of spring 26.

During the foregoing drilling action, a suction is also imposed on lumen 48 of drill shaft 42 (FIG. 2) so that any resultant debris (not shown) produced by drill bit 44 will be drawn into orifice 46 and through drill shaft 42 where it is discharged into the appropriate receptacle. At this point of the discussion of my unique invention, it should be clarified that the entire surgical field on the surface of bone 60 is bathed in a continuous flow of saline solution which keeps the field clear to aid in the vision arthroscopically of the penetration site while simultaneously flushing blood, etc. away from the area. A portion of this saline solution is drawn through the gap between bevel points 21a and 21b into orifice 46 to remove the resultant bone debris generated by the foregoing drilling action.

Figure 5:
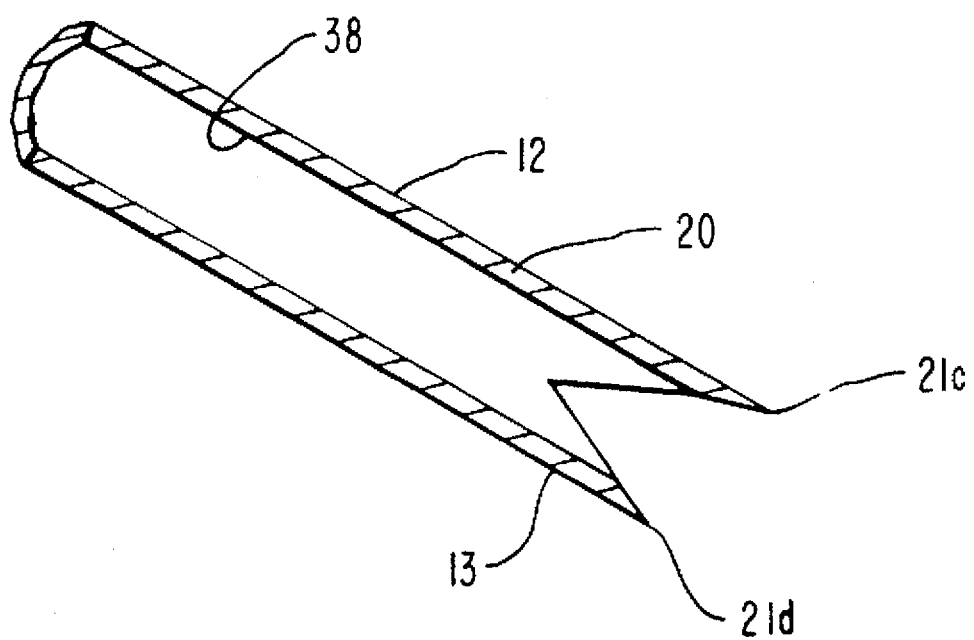
FIG. 5 is a fragmentary, cross-sectional view of the distal end of the shield showing an asymmetric tip on the shield.

Referring now to FIG. 5, a second embodiment of distal end 13 of sheath 14 is shown having a set of asymmetric bevel points 21c and 21d thereon. Bevel point 21c extends incrementally further beyond distal end 13 than bevel point 21d. This unique feature provides the surgeon with certain advantages in that it causes the distal end 13 of sheath 14 to act more like a large-gauge hypodermic needle (not shown) during the penetration of tissue (not shown) by the same. Further, bevel point 21c provides the first contact with the surface of bone 60 (FIGS. 3 and 4) to thereby more precisely position drill bit tip 45 relative to bone 60. With bevel point 21c firmly engaged against bone 60 the surgeon is assured that drill tip 45 will not slip or otherwise skid across the adjacent surface of bone 60 but will penetrate bone 60 at the precise location where shield 12 places drill tip 45.

A further advantage to the asymmetric configuration of bevel points 21c and 21d is that any changes in the angular orientation of bone drill system 10 during the alignment of bone drill 40 will not result in distal end 13 "walking" as might be encountered with the equidistant placement of bevel points 21a and 21b (FIGS. 3 and 4). This so-called "walking" phenomena occurs when bevel points 21a and 21b are brought into contact with the surface of bone 60 and then the angular orientation bone drill system 10 is changed to achieve a different angular orientation for hole 62. This change in angular orientation lifts one of bevel points 21a or 21b away from contact with the surface of bone 60 allowing one of bevel points 21a or 21b to, in effect, take a "step" relative to the other bevel point as sheath 14 is rotated incrementally during the foregoing angular orientation procedure. If repeated several times, this procedure can result in bevel points 21a and 21b causing distal end 13 to literally walk away from the original contact site on the surface of bone 60. Changing distal end to the asymmetric configuration of bevel points 21c and 21d effectively eliminates this problem.

Even through bevel point 21c provides the primary engagement mechanism for bone 60, bevel point 21d provides a useful function in that it extends distally to help screen drill bit 44 and orifice 46 against the adjacent tissue (not shown). Otherwise, if bevel point 21c were alone so that distal end 13 were configured like a conventional single bevel point hypodermic needle (not shown) the adjacent tissue would more readily be drawn against the rotating drill bit 44 and into occluding contact with orifice 46.

The Method

The method of this invention is practiced by the surgeon (not shown) suitably preparing the patient (not shown) and, more specifically, the surface of bone 60 using standard surgical techniques appropriate for the particular surgical procedure being performed. Bone drill system 10 is then mounted to the appropriate drill motor (not shown) and the necessary tubing (not shown) is connected in fluid communication with side port 51. Bone drill system 10 is now ready for use in drilling bone 60.

Bone drill system 10 is inserted through the previously prepared surgical incision (not shown) until the selected bevel points 21a, 21b, or 21c are brought into engagement with bone 60. A controlled amount of pressure exerted against bevel points 21a, 21b, or 21c assures a suitable degree engagement of distal end 13 against bone 60 by the penetration of the surface of bone 60 with bevel points 21a, 21b, or 21c. During this procedure drill tip 45 is also pressed against bone 60 to cause bone drill 40 to be pushed telescopically into sheath 14 and against the spring action of drill spring 26. This displacement of drill tip 45 allows bevel points 21a, 21b, or 21c, as previously discussed, to become firmly seated in the surface of bone 60. The firm seating of distal end 13 of sheath 14 against bone 60 allows the surgeon to activate bone drill 40 and thereby quickly and accurately penetrate drill bit 44 into bone 60 to produce bore 62.

The total depth of bore 62 as determined by the depth of penetration of drill bit 44 into bone 60 is limited by the retraction of sheath 14 relative to the direction of travel of bone drill 40. In particular, forward movement of drill bit 44 into bone 60 causes spring 26 to become compressed by forcing sheath 14 in a rearward direction causing collar 22 to compress spring 26 against the base of end cap 28. Ultimately, proximal end 11 of sheath 14 contacts the corresponding end of tubular boss 29 which acts as a stop against the further rearward travel of sheath 14. Intermediate depths for bore 62 can be selectively controlled by visually observing the movement of indicia 15 into housing 24. In this manner, the surgeon is able to accurately produce bore 62 with the precise, predetermined depth if in the event a depth less than the total allowable depth, as determined by the length of retraction available with sheath 14, is desired.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A bone drill comprising:

a shaft having a distal end and a proximal end;

a drill bit on said distal end of said shaft;

engagement means on said proximal end of said shaft for rotatably engaging said shaft and said drill bit;

a sheath for said shaft and said drill bit, said sheath having a proximal end and a distal end, said sheath comprising a hollow tubular body for telescopically enclosing said shaft and said drill bit;

retraction means on said sheath for telescopically retracting said sheath to cause said drill bit to become extended beyond said distal end of said sheath; and a spring means on said proximal end of said sheath for resiliently urging said distal end of said sheath over said drill bit.

2. The bone drill defined in claim 1 wherein said shaft is hollow having a lumen extending between said distal end of said shaft and said proximal end of said shaft, said shaft including an orifice adjacent said drill bit, said orifice being in fluid communication with said lumen.

3. The bone drill defined in claim 2 wherein said engagement means includes suction means for imposing a negative pressure on said lumen and said orifice.

4. The bone drill defined in claim 1 wherein said sheath includes bone engagement means on said distal end of said sheath for releasably engaging a bone.

5. The bone drill defined in claim 4 wherein said bone engagement means comprises a pair of bevel points formed in said distal end of said sheath, said bevel points providing penetration means for incrementally penetrating bone engaged by said distal end of said sheath to thereby inhibit said drill bit from skidding across the bone.

6. The bone drill defined in claim 5 wherein said pair of bevel points includes a gap means between said bevel points, said gap means admitting fluid flow into said sheath.

7. The bone drill defined in claim 5 wherein said pair of bevel points includes a first bevel point and a second bevel point, said first bevel point extending incrementally further than said second bevel point on said distal end of said sheath, said first bevel point thereby contacting said bone before said second bevel point.

8. The bone drill defined in claim 1 wherein said sheath includes limit means for limiting retraction of said sheath, said limit means thereby limiting the extension of said drill bit beyond said distal end of said sheath.

9. The bone drill defined in claim 8 wherein said sheath includes indicia thereon for visually indicating the extent of retraction of said sheath.

10. The bone drill defined in claim 1 wherein said spring means includes a coiled spring for resiliently urging said sheath against the bone while said drill bit is drilling into the bone.

11. A bone drill with retractable sheath comprising:

a drill shaft having a proximal end and a distal end;

a drill bit on said distal of said drill shaft, said drill bit extending coaxially from said distal end of said drill shaft;

a hollow lumen through said drill shaft;

an orifice in said drill shaft, said orifice being located adjacent said drill bit and in fluid communication with said lumen;

a rigid, tubular sheath telescopically mounted over said drill shaft and said drill bit;

a spring means on said sheath for resiliently urging said sheath over said drill bit into a shielding configuration for said drill bit, said sheath engaging a surface being drilled by said drill bit and being retractable against said spring as said drill bit penetrates said surface.

12. The bone drill defined in claim 11, wherein said spring comprises a coiled spring and a housing for enclosing said coiled spring, said sheath having a proximal end and a distal end with said proximal end extending telescopically inside said housing into engagement with said coiled spring.

13. The bone drill defined in claim 12 wherein said proximal end of said sheath includes a plurality of indicia for providing a visual indication of the extent to which said proximal end of sheath is pushed into said housing against said spring.

14. The bone drill defined in claim 12 wherein said distal end of said sheath includes a pair of bevel points for releasably engaging said distal end of said sheath against a bone to inhibit drill bit from skidding on the bone.

15. The bone drill defined in claim 14 wherein said pair of bevel points comprises a pair of asymmetric bevel points wherein a first bevel point extends incrementally beyond a second bevel point.

16. A method for shielding a bone drill during drilling into bone comprising the steps of:

preparing a sheath for said bone drill, said sheath comprising a hollow tubular element having a proximal end and a distal end;

mounting said proximal end of said hollow tubular element in a housing in sliding relationship to said housing;

incorporating a spring in said housing, said spring resiliently pressing said proximal end of said hollow tubular element;

inserting said bone drill into said sheath;

engaging said distal end of said hollow tubular element against the bone; and drilling the bone with said bone drill while pressing said distal end against the bone thereby forcing said proximal end of said hollow tubular element into said housing against said spring thereby shielding said bone drill as said bone drill is drilling into the bone.

17. The method defined in claim 16 wherein said preparing step includes placing indicia on said sheath for visually indicating the extent to which said sheath is pushed into said housing.

18. The method defined in claim 16 wherein preparing step includes forming bevel points on said distal end of said hollow tubular element, said bevel points engaging the bone thereby inhibiting said bone drill from skidding on the bone.

19. The method defined in claim 18 wherein said forming step includes preparing said bevel points asymmetrically with a first bevel point extending incrementally beyond a second bevel point.

20. The method defined in claim 16 wherein said drilling step includes forming said bone drill with a hollow shaft having an orifice adjacent a drill bit on a distal end of said shaft and applying a suction to said hollow shaft while drilling thereby removing debris produced while drilling the bone with said bone drill.

* * * * *